(12) United States Patent
Leaym et al.

(10) Patent No.: US 7,674,764 B2
(45) Date of Patent: Mar. 9, 2010

(54) CONTROLLED RELEASE COMPOSITIONS

(75) Inventors: Tine Marie Leaym, Saginaw, MI (US); Sylvie Bouzeloc, Montigny-Le-Tilleul (BE); Serge Creutz, Rocourt (BE)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 12/405,495

(22) Filed: Mar. 17, 2009

(65) Prior Publication Data

US 2009/0180977 A1 Jul. 16, 2009

Related U.S. Application Data

(62) Division of application No. 10/548,775, filed as application No. PCT/EP2004/004011 on Mar. 26, 2004, now abandoned.

(30) Foreign Application Priority Data

Mar. 27, 2003 (GB) .................. 0306995.2
Sep. 20, 2003 (GB) .................. 0322044.9

(51) Int. Cl.
*C11D 3/16* (2006.01)
(52) U.S. Cl. ............... 510/466; 512/2; 514/772
(58) Field of Classification Search ........... 510/466; 512/2; 514/772
See application file for complete search history.

(56) References Cited

U.S. PATENT DOCUMENTS

| 4,973,422 | A  | 11/1990 | Schmidt |
| 5,160,494 | A  | 11/1992 | Krzysik et al. |
| 5,246,703 | A  | 9/1993  | Durfee |
| 5,679,335 | A  | 10/1997 | Legrow et al. |
| 6,050,129 | A  | 4/2000  | Shefer |
| 6,083,900 | A  | 7/2000  | Auguste et al. |
| 6,294,634 | B1 | 9/2001  | Ferritto et al. |
| 2005/0124530 | A1 | 6/2005 | Creutz et al. |
| 2005/0143282 | A1 | 6/2005 | Creutz et al. |

FOREIGN PATENT DOCUMENTS

| EP | 0118625 | 3/1989 |
| EP | 0908174 | 4/1999 |
| JP | 01/294612 | 11/1989 |
| JP | 07/041413 | 2/1995 |
| WO | WO94/07461 | 4/1994 |
| WO | WO96/19119 | 6/1996 |
| WO | WO98/28396 | 7/1998 |
| WO | WO98/41607 | 9/1998 |
| WO | WO00/02981 | 1/2000 |
| WO | WO01/25389 | 4/2001 |

*Primary Examiner*—John R Hardee
(74) *Attorney, Agent, or Firm*—Alan Zombeck

(57) ABSTRACT

A composition for controlled release of an active material such as a fragrance, sunscreen, vitamin or biocide in a product such as a hair shampoo, shower gel, another personal product such as an antiperspirant or deodorant, a household cleaning product such as a laundry detergent, hard surface cleaner or polishes, or a fabric softener, air freshener or tumble drier sheet, comprises a blend of the active material and a waxy cyclopolysiloxane. The cyclopolysiloxane is preferably substituted by hydrocarbon substituents having 12 or more carbon atoms and may also contain an aryl or aralkyl substituent.

2 Claims, No Drawings

CONTROLLED RELEASE COMPOSITIONS

The present application is a divisional application of U.S. patent Ser. No. 10/548,775, now abandoned, filed Sep. 8, 2005 as a national stage application under 35 USC 371 which claimed priority from PCT Application No. PCT/EP2004/004011 filed on Mar. 26, 2004, which claimed priority from GB 0306995.2 filed Mar. 27, 2003 and GB 0322044.9 filed on Sep. 20, 2003. The above identified applications are incorporated by reference in their entirety.

This invention relates to compositions and processes for the controlled release of active materials suitable for incorporation in personal care products such as hair shampoos and soaps and shower gels for personal washing, in other personal care products such as antiperspirants or deodorants, in cleaning compositions such as laundry detergents, hard surface cleaners or wiping cloths, in other household care products such as polishes or air fresheners, or in textile treatment compositions such as fabric softeners or tumble drier sheets.

One type of active material for which controlled release is desired is a fragrance composition. Fragrances are frequently incorporated in detergents and other cleaning products to give a pleasant odor during use of the cleaning product and to mask the inherent smell of the soap or other surfactant present in the cleaning product. The fragrances are generally complex mixtures of fragrant compounds of varying volatility. Upon storage in a cleaning composition, perfumes and fragrances can be altered through interactions and/or reactions with the other components of the composition. Due to their volatile nature, the fragrant compounds tend to be dissipated with time, particularly the most volatile compounds which are often associated with perceived freshness. Moreover, when used, such as during washing of fabrics with a laundry detergent, most of the perfume is also lost in the aqueous phase during the washing cycle. It has been recognised as desirable that the fragrance should survive storage in the cleaning composition and also survive the cleaning process and should be deposited on the fabric, so that fabrics laundered with a detergent containing the fragrance should have the pleasant odor of the fragrance.

Furthermore, once adsorbed onto the targeted surface, for example fabrics or hair or skin, the fragrance tends to be dissipated very quickly. There is thus a need to improve the storage stability of perfumes and fragrances, their delivery in the application and their long-lasting effect through sustained delayed release once applied on fabrics.

Various methods of protecting the fragrance composition have been proposed. The perfume may be mixed with a porous carrier such as zeolite and then coated with a protective barrier, for example a sugar derivative before incorporation in a laundry detergent as described in WO98/41607. U.S. Pat. No. 4,973,422 describes encapsulating perfume particles with a pH sensitive coating comprising an acrylic resin and cellulose esters. WO-A-98/28936 describes mixing the perfume with an aqueous slurry of polymer beads made of hydrophobic polyacrylate; polyvinyl alcohol can be adsorbed at the surface of the beads to improve deposition. WO-A-00/02981 describes reacting a perfume component with an amine to obtain a release of the active component over a longer period of time.

U.S. Pat. No. 6,050,129 relates to a process for testing diffusivity, odor character and odor intensity of a fragrance material used in an air freshener and describes mixing perfume with a hydrophobic wax such as candelilla wax or carnauba wax and emulsifying the blend in water, preferably with cationic surfactants, to form a long lasting fragrance composition for use in a hair care composition such as a shampoo/conditioner.

WO-A-01/25389 describes a domestic care product comprising a fragrance particle. The particle comprises a fragrance composition and a silicone polymer having a melting point of at least 10° C. At least 20% of the silicone atoms in the silicone polymer have a substituent of 16 carbon atoms or more.

U.S. Pat. No. 5,160,494 describes a perfume composition comprising a perfume oil and a volatile alkylmethylsiloxane, which may be a short chain linear alkylmethylsiloxane or a cyclic alkylmethylsiloxane.

JP-A-1-294612 describes a makeup cosmetic such as lipstick, foundation, eye shadow or sunstick containing a cyclic poly(methyl 16-30C alkyl siloxane) wax to impart waxy properties to the cosmetic. JP-A-7-41413 describes a makeup cosmetic containing the same cyclic polysiloxane wax and an alkyl-modified silicone oil to impart superior cosmetic holding. There is no suggestion in these patents of controlled release of any ingredient.

EP-A-908174 describes a fragrance composition comprising ellipsoidal hydrophobic particles consisting of a single phase solid solution of a hydrophobic polymer or wax of melting point 35-120° C. having dissolved therein a hydrophobic fragrance material, and a hydrophilic surfactant proximate to the outer surface of the particles.

According to the present invention a process for controlling the release of an active material, selected from fragrances, sunscreens, vitamins, drugs, biocides, pest repellents, catalysts and cooling agents, from a cleaning composition, personal care product, household care product or textile treatment composition by blending the active material and a waxy silicone material before adding the active material to the cleaning composition, personal care product, household care product or textile treatment composition, is characterised in that the waxy silicone material is a cyclopolysiloxane substituted by hydrocarbon substituents having 12 or more carbon atoms.

One example of an active material is a fragrance composition. The fragrance composition may be solid or liquid and may be a single fragrant compound, or a natural scented oil, or may be a mixture of fragrant compounds and/or natural oils. Examples of such natural oils and fragrant compounds are described in WO-A-01/25389; these natural oils and fragrant compounds are in particular those suitable for use in cleaning compositions for household or personal use, or for air fresheners. The fragrance composition may be a perfume for incorporation in a personal care product such as a skin cream, shampoo or face cream, or may be a flavour or aroma compound to be applied for example to food or food packaging. Flavour compounds, for example fruit flavours such as strawberry essence, can also be applied to toys or other objects. The fragrance composition can alternatively comprise a chemically protected fragrance compound such as a reaction product of the fragrance compound.

An alternative type of active material which can be incorporated in the controlled release composition is a sunscreen composition. Examples of sunscreens include those which absorb ultraviolet light between about 290-320 nanometers (the UV-B region) such as para-aminobenzoic acid derivatives and cinnamates such as octyl methoxycinnamate or 2-ethoxyethyl p-methoxycinnamate; and those which absorb ultraviolet light in the range of 320-400 nanometers (the UV-A region) such is benzophenones and butyl methoxy dibenzoylmethane. Additional examples of sunscreen chemicals which may be used as active material in the present invention include menthyl anthranilate; homomenthyl salicylate; glyceryl p-aminobenzoate; isobutyl p-aminobenzoate; isoamyl p-dimethylaminobenzoate; 2,2'-dihydroxy-4-methoxybenzophenone; 2-hydroxy-4-methoxybenzophenone; 4-mono and 4-bis(3-hydroxy-propyl)amino isomers of ethyl benzoate; and 2-ethylhexyl p-dimethylaminobenzoate. The invention is particularly applicable to lipophilic screening agents, including the family of screening agents derived from dibenzoylmethane and more especially 4-tert-butyl-4'-methoxydibenzoylmethane, which effectively have a high intrinsic power of absorption. These dibenzoylmethane derivatives are well known as UV-A active screening agents and are described in particular in European patent application EP-A-0,114,607. 4-(tert-butyl)-4'-methoxydibenzoylmethane is sold under the trade mark "Parsol 1789" by Givaudan. Another dibenzoylmethane derivative which is preferred according to the present invention is 4-isopropyldibenzoylmethane, sold under the name "Eusolex 8020" by Merck. Octocrylene, a liquid lipophilic screening agent known for its activity in the UV-B range and sold under the trade mark "Uvinul N 539" by BASF. Another lipophilic (or liposoluble) screening agent which can be used in the invention is p-methylbenzylidenecamphor, which is known as a UV-B absorber and is sold under the trade name "Eusolex 6300" by Merck. The sunscreen can alternatively be a hydrophilic screening agent, for example one or more of those described in Application EP-A-678,292, particularly a 3-benzylidine-2-camphorsulphonic derivative such as benzene-1,4-[di(3-methylidenecamphor-10-sulphonic acid)], known under the trade name Mexoryl SX, or a sulphonic derivative of benzophenone or 2-phenylbenzimidazole-5-sulphonic acid, for example that sold under the trade mark "Eusolex 232" by Merck, benzene-1,4-di(benzimidazol-2-yl-5-sulphonic acid) or benzene-1,4-di(benzoxazol-2-yl-5-sulphonic acid).

An alternative type of active material which can be incorporated in the controlled release composition is a vitamin composition. Vitamins are a class of organic compounds that must be ingested part of the diet for humans (and other organisms) in order to maintain health and well being. Some vitamins also have beneficial effects when applied topically and for this reason are popular ingredients in various personal care formulations, where it is desired that the vitamin should be released gradually after the formulation has been applied to the skin or hair.

Vitamins comprise a variety of different organic compounds such as alcohols, acids, sterols, and quinones. They can be classified into two solubility groups: lipid-soluble vitamins and water-soluble vitamins. Lipid-soluble vitamins that have utility in personal care formulations include retinol (vitamin A), ergocalciferol (vitamin $D_2$), cholecalciferol (vitamin $D_3$), phytonadione (vitamin $K_1$), and tocopherol (vitamin E). Water-soluble vitamins that have utility in personal care formulations include ascorbic acid (vitamin C), thiamin (vitamin $B_1$) niacin (nicotinic acid), niacinamide (vitamin $B_3$), riboflavin (vitamin $B_2$), pantothenic acid (vitamin $B_5$), biotin, folic acid, pyridoxine (vitamin $B_6$), and cyanocobalamin (vitamin $B_{12}$). The present invention is particularly useful in giving controlled release of lipid-soluble vitamins but can also give controlled release of some water-soluble vitamins. Examples of vitamins which have been blended with a waxy cyclopolysiloxane to give controlled release are vitamins A and E.

Many of the vitamins that are used in personal care compositions are inherently unstable and therefore present difficulties in the preparation of shelf-stable personal care compositions. The instability of the vitamins is usually related to their susceptibility to oxidation. For this reason, vitamins are often converted into various derivatives that are more stable in personal care formulations. These vitamin derivatives offer other advantages in addition to improved stability. Vitamin derivatives can be more amenable to certain kinds of personal care formulations. For example a lipid-soluble vitamin can be derivatized to produce a water-soluble material that is easier to incorporate into a water-based formulation. Retinol and tocopherol are two lipid-soluble vitamins that are particularly useful in skin care compositions and consequently there are many different derivatives of these two vitamins that are used in personal care compositions. Derivatives of retinol include retinyl palmitate (vitamin A palmitate), retinyl acetate (vitamin A acetate), retinyl linoleate (vitamin A linoelate), and retinyl propionate (vitamin A propioniate). Derivatives of tocopherol include tocopheryl acetate (vitamin E acetate), tocopheryl linoleate (vitamin E linoleate), tocopheryl succinate (vitamin E succinate), tocophereth-5, tocophereth-10, tocophereth-12, tocophereth-18, tocophereth-50 (ethoxlyated vitamin E derivatives), PPG-2 tocophereth-5, PPG-5 tocophereth-2, PPG-10 tocophereth-30, PPG-20 tocophereth-50, PPG-30 tocophereth-70, PPG-70 tocophereth-100 (propoxylated and ethoxylated vitamin E derivatives), and sodium tocopheryl phosphate. The invention can be used to give controlled release of these vitamin derivatives. Derivatives of ascorbic acid (Vitamin C) such as ascorbyl palmitate, ascorbyl dipalmitate, ascorbyl glucoside, ascorbyl tetraisopalmitate, and tetrahexadecyl ascorbate can also be used as the active material, as can vitamin derivatives incorporating two different vitamins in the same compound, for example ascorbyl tocopheryl maleate, potassium ascorbyl tocopheryl phosphate or tocopheryl nicotinate.

A further alternative type of active material which can be incorporated in the controlled release composition is a biocide, for example to give prolonged protection of a composition against bacterial degradation or to give a prolonged biocidal effect to a substrate to which the composition has been applied. The active material can also be a pest repellent, for example an insect repellent, or a repellent for rodents, or a repellent for any animal including cats or dogs. Insect repellent personal care products can for example be in the form of creams, sticks or sprays, and controlled release of the insect repellent from the personal care product is required after the product has been applied to the skin.

A further alternative type of active material which can be incorporated in the controlled release composition is a catalyst, for example a curing catalyst in coatings or adhesives where controlled release is advantageous to give thorough cure without curing too rapidly. One example of such a catalyst is a fatty amine to be used as curing agent for an epoxy resin composition.

The invention can also be used to give controlled release of a cooling agent (a material which gives a cooling sensation to the skin) such as menthol or other cooling agents described in WO96/19119. The blend of cooling agent and waxy cyclopolysiloxane material can be incorporated in a skin care composition to give prolonged release of the cooling agent when the composition is rubbed into the skin. The invention can also be used to give controlled release of a drug (a pharmaceutically active material) from a composition which is applied to the skin to dose the drug by transdermal delivery.

The invention is particularly applicable to hydrophobic lipophilic active materials, since these are more readily miscible with the waxy cyclopolysiloxanes and are less readily released from blends with waxy cyclopolysiloxanes, but the invention is also effective in giving controlled release of hydrophilic active materials provided these are not so hydrophilic that they have a high solubility in water.

We have found that the waxy cyclopolysiloxanes tend to be more miscible with the active materials, and in particular with perfume compounds, than linear polysiloxane waxes are. We have also found that the waxy cyclopolysiloxanes tend to provide a longer lasting effect, that is a more sustained release of the fragrance or sunscreen or vitamin.

The waxy cyclopolysiloxane generally contains hydrocarbon substituents having 12 or more carbon atoms. The waxy cyclopolysiloxane preferably comprises methyl alkyl siloxane units ((CH3)(R')SiO2/2), where R' is a long chain alkyl group having 12 or more, preferably 16 to 100 carbon atoms. The long chain alkyl group R' can optionally be substituted by polar substituents such as amino, amido, alcohol, alkoxy, or ester groups. All the siloxane units of the waxy cyclopolysiloxane may be such methyl alkyl siloxane units, or the waxy cyclopolysiloxane may additionally contain dimethyl siloxane units or units of the formula $((CH_3)(R'')SiO_{2/2})$ where R" is an alkyl group having 1-11 carbon atoms, for example ethyl, a cycloalkyl group such as 2-cyclohexylethyl, a haloalkyl group or an aromatic group. The methyl group of the above siloxane units could be replaced by ethyl or another lower alkyl group if desired. Preferably at least 20% of the silicon atoms in the polysiloxane, and most preferably at least 50%, have an alkyl substituent having 16 to 100 carbon atoms, most preferably 20 to 45 carbon atoms. The cyclopolysiloxane is preferably a cyclotetrasiloxane or cyclopentasiloxane or a mixture thereof. One preferred type of waxy cyclopolysiloxane contains aromatic groups, for example aryl groups attached directly to Si such as phenyl, or aralkyl groups comprising phenyl or substituted phenyl groups attached to silicone through an alkylene linkage, in addition to long chain alkyl groups. Waxy cyclopolysiloxanes containing aralkyl groups, that is, silicon-bonded substituents of the formula X—Ph, wherein X denotes a divalent aliphatic organic group bonded to silicon through a carbon atom and Ph denotes an optionally substituted aromatic group, are particularly preferred, for example 2-phenylpropyl, benzyl, 2-phenylethyl or 2-(t-butylphenyl)ethyl. Such aralkyl groups may for example be present in 10 to 80%, preferably 20 to 50% of the siloxane units of the waxy cyclopolysiloxane, usually as methyl aralkyl siloxane units. The waxy cyclopolysiloxane preferably has a melting point in the range 10-200° C., most preferably 30 to 80° C.

The waxy cyclopolysiloxane can in general be produced by the reaction of a cyclopolysiloxane containing SiH groups such as tetramethylcyclotetrasiloxane or pentamethylcyclopentasiloxane with a long chain alpha-olefin of the formula R'CH=CH$_2$ in the presence of a hydrosilylation catalyst such as a platinum group metal compound. Aralkyl and/or cycloalkyl groups can be introduced by the reaction of such compounds as alpha-methylstyrene, styrene or vinylcyclohexane with the cyclopolysiloxane before, simultaneously with or following reaction of the long chain alpha-olefin. The waxy cyclopolysiloxane may contain some residual SiH groups, or any such residual SiH groups can be reacted with a short chain olefin, for example with ethene to introduce ethyl groups. The waxy cyclopolysiloxane can be produced by the addition of olefin(s) sequentially or concurrently to SiH containing silicone or by the addition of SiH to olefin(s).

The waxy cyclopolysiloxanes containing aralkyl groups are new materials. The invention thus includes a wax of melting point 10-200° C. which is a cyclopolysiloxane in which at least 20% of the silicon atoms in the cyclopolysiloxane have an alkyl substituent having 16 to 100 carbon atoms and 10 to 80% of the silicon atoms of the cyclopolysiloxane have a silicon-bonded substituent of the formula X—Ph, wherein X denotes a divalent aliphatic organic group bonded to silicon through a carbon atom and Ph denotes an aromatic group.

The waxy cyclopolysiloxane can be mixed with a liquid silicone, for example a polydiorganosiloxane, a branched liquid polysiloxane, a silicone polyether copolymer or an aminopolysiloxane. Particularly preferred liquid polysiloxanes are those containing aryl, for example phenyl, or aralkyl, for example benzyl, 2-phenylethyl or 2-phenylpropyl groups in addition to alkyl groups such as methyl. The liquid polydiorganosiloxane can be linear or cyclic; cyclic siloxanes such as tetra(2-phenylpropyl)tetramethylcyclotetrasiloxane may be preferred. The liquid polysiloxane can contain functional groups, for example it can contain hydroxyl groups such as terminal silanol groups in a linear polydiorganosiloxane such as polydimethylsiloxane, alkoxy groups such as methoxy, ethoxy or propoxy bonded to silicon, or amino, amido, alcohol or alkoxy groups substituted in an organic group bonded to silicon. The waxy hydrophobic mixture of the waxy cyclopolysiloxane and the liquid silicone is preferably a solid, for example it preferably has a melting point in the range 10-200° C., but can alternatively be a viscous liquid. The liquid silicone can for example be used at up to 100% or even higher based on the weight of the wax, such as up to 200 or 300%, particularly if the blend of wax and liquid silicone is solid at 10° C., although the liquid silicone if used is preferably present at 1 to 60%, most preferably 10 to 30%, based on the weight of wax. An organic liquid, for example liquid paraffin or a naphthenic oil, can be used alternatively or additionally if it is compatible with the blend of active material and waxy cyclopolysiloxane.

The blend of active material and waxy cyclopolysiloxane can incorporate a further wax, for example a linear polysiloxane wax or an organic which does not contain silicon, although the waxy cyclopolysiloxane preferably forms at least 50% by weight of the wax component of the blend. Suitable linear polysiloxane waxes generally contain methyl alkyl siloxane units ((CH3)(R')SiO2/2) as described above and can contain other substituents such as aralkyl, aryl, alkyl or cycloalkyl groups as described above for the waxy cyclopolysiloxane.

In one preferred form of the invention the composition for controlled release of active material, for example fragrance, forms the disperse phase of an oil-in-water emulsion. Most preferably, the continuous phase of the emulsion comprises an aqueous solution of concentration at least 0.1 molar of a salt capable of ionic disassociation in water. We have found that the high ionic strength of the continuous phase increases the partition coefficient between the continuous phase and the waxy cyclopolysiloxane matrix, so that the active material tends to stay in the wax phase rather than diffusing into the continuous phase.

The salt present in the continuous phase can for example be an alkali metal, ammonium or alkaline earth metal salt. It can be an inorganic salt such as a chloride, sulphate or phosphate but is preferably an organic salt, particularly a carboxylate. The salt can be a monocarboxylate such as an acetate or propionate, for example sodium acetate, or a di- or polycarboxylate salt, for example a succinate, phthalate or citrate. The salt can be a polyelectrolyte, for example a salt of a polymeric acid such as a polycarboxylate, e.g. a polyacrylate or polymethacrylate or a salt of an acrylic or methacrylic acid copolymer. Examples of such polyelectrolyte salts are sold under the Trade Mark 'Sokolan'. The salt in the continuous phase can alternatively be a salt of a polycation such as a polymer having pendant quaternary ammonium groups. An example of such a cationic polymer is sold under the Trade Mark 'Merquat' and contains dimethyl diallyl ammonium chloride or methacrylamidopropyl trimethyl ammonium chloride groups. The salt preferably has no surfactant properties; in general, the salt should not contain any organic group which has a chain of 8 or more carbon atoms unsubstituted by polar groups. The concentration of the salt in the aqueous solution which forms the continuous phase of the emulsion is preferably at least 0.1 M (molar), more preferably at least 1 M, up to 5 or 10 M. In the case of a salt of a polyelectrolyte, the concentration is measured as the concentration of the non-polymeric ion of the salt.

The emulsion can conveniently be formed by melting the blend of active material and waxy cyclopolysiloxane, and liquid silicone if used, and emulsifying it in the continuous phase using at least one surfactant. The surfactant is preferably immiscible with the said blend. The surfactant can be a cationic, anionic, nonionic or amphoteric surfactant, although the ionic surfactants are more likely to be immiscible with a perfume wax blend. Cationic surfactants are particularly preferred because of their propensity to adsorb at surfaces, in particular onto fabrics. Examples of suitable cationic surfactants include alkylamine salts, quaternary ammonium salts, sulphonium salts and phosphonium salts. Especially preferred cationic surfactants are quaternary ammonium materials containing at least one ester group ("esterquats"). The ester group is preferably a linking group in the quaternary ammonium molecule. Preferred esterquats comprise a quaternary ammonium moiety containing one, two or three higher molecular weight groups, for example of 12 to 22 carbon atoms, containing at least one ester linkage, and three, two or one lower molecular weight alkyl groups. Such esterquats are described in U.S. Pat. No. 4,137,180, for example 1,2-bis(hardened tallowoyloxy)-3-trimethylammonium-propane chloride and/or 1-hardened tallowoyloxy-2-hydroxy-3-trimethylammonium-propane chloride, di(tallowoyloxy-ethyl) dimethyl ammonium chloride, or di(tallowoyloxyethyl) methyl hydroxyethyl methosulphate. We have found that use of esterquat surfactants in the emulsion of active material and waxy cyclopolysiloxane can reduce the level of silicone wax needed to give controlled fragrance delivery, for example in a rinse cycle softener used in home laundry.

The emulsion can alternatively be made by emulsifying the waxy cyclopolysiloxane in the absence of the active material. The active material, for example a fragrance or sunscreen composition is post-added to the emulsion, which is then heated above the melting point of the waxy cyclopolysiloxane and left standing at this temperature, preferably for a period of at least 10 minutes, for example 30-60 minutes, allowing the active material to diffuse within the hydrophobic waxy cyclopolysiloxane droplet.

The composition for controlled release of active material can be produced in various forms. For example in the case of fragrances, for some applications the controlled release fragrance composition can simply be mixed with a cleaning or cosmetic composition. The controlled release fragrance composition can be produced in particulate form, which may be preferred for blending with a solid cleaning product such as a powder detergent. An emulsion as described above can be deposited on a particulate solid carrier or can be spray dried. Alternatively the blend of fragrance composition, waxy cyclopolysiloxane and optionally liquid silicone can be melted and the melt can be deposited on a particulate solid carrier or can be spray dried. Examples of suitable solid carriers include soda ash (sodium carbonate), zeolites and other aluminosilicates or silicates, for example magnesium silicate, phosphates, for example powdered or granular sodium tripolyphosphate, sodium sulphate, sodium carbonate, sodium perborate, cellulose derivatives such as sodium carboxymethylcellulose, granulated or native starch and clay.

The carrier particles are preferably mixed while being treated in a granulation process which produces agglomerated granules. In one preferred process, the particles are agitated in a vertical, continuous high shear mixer in which an emulsion of the composition for controlled release of fragrance is sprayed onto the particles. If needed to improve the granulation process, the emulsion can be diluted with for example water, molten polyethylene glycol or an aqueous solution of polyelectrolyte. One example of such a mixer is a Flexomix mixer supplied by Hosokawa Schugi. The spraying and mixing produces agglomerated granules. Alternative mixers may be used, for example horizontal mixers such as pin mixers or paddle mixers, ploughshare mixers, twin counter-rotating paddle mixers, or intensive mixers including a high shear mixing arm within a rotating cylindrical vessel. Alternatively a fluid bed coating procedure can be used. Advantageously a process of granulation by mixing can be followed by cooling and drying in a continuous fluid bed.

Granules produced from an emulsion whose continuous phase is an aqueous solution of a polyelectrolyte salt may be post-coated with a material, for example a polymer, of opposite charge to the polyelectrolyte. If the salt in the continuous phase of the emulsion is a cationic polyelectrolyte salt, for example, the granules can be post-coated with an anionic polyelectrolyte. Such post-coating may improve the deposition of the perfume on a fabric which is subsequently washed or rinsed in the presence of the granules.

Granules with a perfume content of up to 15%, for example 8-12%, by weight can readily be produced by the process of the invention. An emulsion according to the invention can have a perfume content of up to 30 or 40% or even 50% by weight.

In an alternative process according to the invention for producing a fragrant powdered cleaning product, the emulsion described above is deposited on a powdered cleaning product, for example by spraying the emulsion onto a detergent powder composition, and is subsequently dried.

In a process according to the invention for producing a fragrant liquid cleaning product, for example a liquid laundry detergent, household cleaning product, fabric softener, hair shampoo or soap or shower gel for personal washing, or a roll-on or spray deodorant, an emulsion as described above is dispersed in the liquid cleaning product, or the blend of a fragrance composition, waxy cyclopolysiloxane and optionally liquid silicone can be emulsified in the liquid cleaning product. When producing a cleaning product or personal care product in gel form, for example a stick deodorant, an emulsion as described above can be incorporated in the product when it is in liquid form, or the blend of a fragrance composition, wax and liquid silicone can be emulsified in the product when it is in liquid form, before it is gelled. A tumble drier sheet can be produced by impregnating a textile material with an emulsion as described above.

A textile treatment composition according to the present invention may be any composition for treating fibrous material including leather or paper as well as natural or synthetic fibre textile materials such as woven, nonwoven or knitted fabrics. In addition to tumble drier sheets mentioned above, release of fragrance can be controlled from fabric softeners, fabric and garment finishing compositions, leather finishing compositions or paper tissue for personal or household cleaning use. Release of drugs (pharmaceutically active materials) such as menthol or camphor can be controlled from handkerchiefs or tissues.

The delayed release fragrance composition of the invention can alternatively be applied as a coating to a substrate to give sustained release of perfume from the surface. The coating can for example be an emulsion as described above.

Where the active material is a sunscreen composition, the controlled release composition can for example be prepared in the form of an emulsion as described above. The emulsion can then be mixed into a skin care or other cosmetic composition, or into a fabric care composition. For example, a lipophilic screening agent(s) can be present in a skin care composition according to the invention at 0.5 to 30%, preferably from 0.5 to 20%, of the total weight of the composition. A hydrophilic screening agent(s) can be present in the skin care composition at 0.1 to 20%, preferably from 0.2 to 10%, by weight of the composition. The skin care composition can additionally contain pigments, preferably nanopigments (average primary particle size: generally between 5 nm and 100 nm, preferably between 10 and 50 nm) of coated or uncoated metal oxides, such as nanopigments of titanium oxide (amorphous or crystallized in rutile and/or anatase form), of iron oxide, of zinc oxide, of zirconium oxide or of cerium oxide, which are all photoprotective agents which act by physically blocking (reflection and/or scattering) UV radiation. Examples of coating agents for the metal oxide pigments are alumina and/or aluminum stearate, and silicones.

The advantages of incorporating a UV absorbing sunscreen in a laundry detergent are described in a paper by M. Schaumann et al entitled "Sun Protection via Laundry Products" presented at 5$^{th}$ World Conference on Detergents, 13-17 Oct. 2002 in Montreux, Switzerland. The UV transmittance of a fabric is reduced by washing in such a detergent. It is desirable that the sunscreen should survive storage in the cleaning composition and should not be lost in the aqueous phase during the washing cycle so that it is deposited on the fabric. Blending the sunscreen with a waxy cyclopolysiloxane according to the invention increases the proportion of sunscreen deposited on the fabric.

The invention is illustrated by the following Examples:

EXAMPLE 1

A waxy cyclopolysiloxane (WCP) of melting point 50° C. was prepared by reacting an olefin mixture consisting of 50% by weight C26 and C28 olefins and 50% alpha-methylstyrene with tetramethylcyclotetrasiloxane (cyclic SiH compound). The waxy cyclopolysiloxane was miscible in weight ratio 1:1 with the fragrance compounds benzaldehyde, benzyl acetate or cineole. The waxy cyclopolysiloxane was melted and blended with an equal weight of cineole. The blend was then placed in an oven at 35° C. for a weight loss assessment.

In a comparative experiment 1a, a linear silicone wax (LSW) was prepared by reacting a linear poly(methylhydrogensiloxane) having a degree of polymerisation of 60 units with the same olefin mixture. The wax produced had melting point 63° C. and was not miscible in weight ratio 1:1 with benzaldehyde or benzyl acetate. The wax was melted and blended with an equal weight of cineole and placed in an oven at 35° C. for a weight loss assessment. The results are shown in Table 1 below.

TABLE 1

| Systems | Ratios | | Time (days) | | | |
|---|---|---|---|---|---|---|
| | | | 1 | 3 | 6 | 16 |
| pure cineole | — | Residual perfume percentage | 0.0 | 0.0 | 0.0 | 0.0 |
| Example 1a cineole/LSW | 1/1 | | 49.0 | 10.0 | 3.4 | 2.3 |
| Example 1 cineole/WCP | 1/1 | | 73.4 | 56.1 | 42.1 | 22.5 |

Table 1 clearly shows that the waxy cyclopolysiloxane gave a more prolonged release of cineole than the linear silicone wax.

EXAMPLE 2

A waxy cyclopolysiloxane (WCP 2) of melting point 66° C. was prepared by reacting an olefin mixture consisting predominantly of C26 and C28 olefins with tetramethylcyclotetrasiloxane. 20 g of the waxy cyclopolysiloxane was melted and blended with 5 g cineole. The blend was then placed in an oven at 35° C. for a weight loss assessment, the results of which are shown in Table 2.

TABLE 2

| Systems | Ratios | | Time (days) | | |
|---|---|---|---|---|---|
| | | | 5 | 14 | 21 |
| cineole/WCP2 | 1/4 | Residual perfume percentage | 88.1 | 44.9 | 27.0 |

EXAMPLE 3

8 g of cineole, 32 g of the waxy cyclopolysiloxane prepared in Example 2, 25 g of a cationic polymer sold under the Trade Mark 'Merquat 2001 N' which contains methacrylamidopropyl trimethyl ammonium chloride groups, 13.5 g of Arquad 16-29 cationic surfactant and 6.0 g of NaCl were weighed in a reactor and heated to 70° C. When the mixture was molten, it was emulsified and diluted with 50 g of water to produce an emulsion having a disperse phase of a blend of cineole and waxy cyclopolysiloxane in an aqueous continuous phase having high ionic strength from the dissolved NaCl and 'Merquat 2001 N'.

0.42 g of the emulsion was pre-mixed with 1.42 g of fabric softener based on a cationic surfactant and then diluted with 350 mL of soft water. 70 mL of this solution was poured in a Büchner funnel equipped with a piece of towel as filter (about 3.00 g of towel). The towel was then line dried and the odor intensity was monitored subjectively in a panel test. In a comparative test, the same process was followed using 0.025 g of pure perfume instead of the emulsion. The odor of the sample with free perfume is perceivable during approximately 1.5 hours while the odor of the sample with perfume blended with waxy cyclopolysiloxane is perceivable during about 24 h.

EXAMPLES 4 AND 5

16 g and 24 g respectively of the waxy cyclopolysiloxane of Example 2 were melted and blended with 4 g benzaldehyde.

EXAMPLE 6

5 g of benzaldehyde was blended with 10 g of the waxy cyclopolysiloxane of Example 2 and 10 g of a liquid phenyl (trimethylsiloxy)silane sold under the Trade Mark 'Dow Corning DC 556'.

EXAMPLE 7

16 g of the silicone wax was melted and blended with 4 g benzaldehyde and 8 g DC556 liquid silicone.

EXAMPLE 8

A liquid silicone consisting mainly of tetra(2-phenylpropyl)tetramethylcyclotetrasiloxane was prepared by reacting alpha-methylstyrene with tetramethylcyclotetrasiloxane. 10 g of the waxy cyclopolysiloxane wax of Example 2 was melted and blended with 5 g benzaldehyde and 10 g of the liquid silicone prepared above.

Each of the blends of Examples 4 to 8 was then placed in an oven at 35° C. for a weight loss assessment. The results are shown in Table 3.

TABLE 3

| Systems | Ratios | | Time (days) | | | |
|---|---|---|---|---|---|---|
| | | | 1 | 2 | 8 | 15 |
| pure benzaldehyde (BZA) | — | Residual perfume percentage | 26.1 | 24.7 | 21.8 | 19.9 |
| Example 4 (BZA/wax) | 1/4 | | 87.4 | 68.9 | 8.7 | 3.9 |
| Example 5 (BZA/wax) | 1/6 | | 96.0 | 83.8 | 31.8 | 14.1 |
| Example 6 (BZA/wax/liquid) | 1/2/2 | | 99.0 | 85.8 | 27.8 | 6.2 |
| Example 7 (BZA/wax/liquid) | 1/4/2 | | 98.0 | 94.7 | 52.7 | 24.5 |
| Example 8 (BZA/wax/liquid) | 1/2/2 | | 94.2 | 79.9 | 31.5 | 14.4 |

EXAMPLE 9

A suncare composition was prepared by combining the following components utilizing conventional mixing techniques.

TABLE 4

| Ingredient | Wt. % | Trade Name/Supplier |
|---|---|---|
| 1. Cyclopentasiloxane (and) PEG/PPG-18/18 Dimethicone | 11 | Dow Corning ® 5225C FORMULATION AID |
| 2. Cyclomethicone | 8 | Dow Corning ® 245 FLUID |
| 3. Dow Corning ® waxy Cyclopolysiloxane containing alkyl substituents and Aryl substituents in emulsion form | 4 | |
| 4. Octyl Methoxycinnamate sunscreen | 7 | Parsol ® MCX/Roche Vitamins Inc. |
| 5. Zinc Oxide (and) Dimethicone | 5 | Z-Cote HP-1/BASF |
| 6. Butylene Glycol/Sea Parsley Extract | 0.5 | Sea Parsley/Collaborative Group |
| 7. Sodium Chloride | 2 | |
| 8. Polysorbate 20 | 0.4 | Tween 20 Enzyme Grade/Fisher Chemical Company |
| 9. Water (and) cyclomethicone (and) Liquorice extract (and) Butylene glycol (and) Phospholipids | 3 | Melarrest/Collab. Lab. |
| 10. Deionised Water | 58.8 | |
| 11. Diazolidinyl urea/propylene glycol/iodopropynul butylcarbamate | 0.5 | Liquid Germal Plus/ISP |

The waxy cyclopolysiloxane (3) was melted and blended with the sunscreen (4). The resulting blend was emulsified at a temperature above the melting point of the waxy cyclopolysiloxane in an aqueous phase comprising ingredients (6) to (10). The Z-Cote (5) was added to a mixture of the siloxane fluids (1 and 2) and mixed until homogeneous, then added to the emulsion with turbulent mixing. The biocide (11) was added and mixing was continued for 15 minutes

EXAMPLE 10

A suncare composition was prepared by combining the following components utilizing conventional mixing techniques.

TABLE 5

| Ingredient | Wt. % | Trade Name/Supplier |
|---|---|---|
| 1. Sucrose Palmitate & Glyceryl Stearate & Glyceryl Stearate Citrate & Sucrose & Mannan & Xanthan Gum | 1 | Arlatone V-175/Uniqema |

TABLE 5-continued

| Ingredient | Wt. % | Trade Name/Supplier |
|---|---|---|
| 2. Deionised Water | 65.2 | |
| 3. Glycerin | 5 | Glycerin/Lambert Riviere |
| 4. Methyldibromoglutaronitrile & Phenoxyethanol | 0.7 | Euxyl K400/S&M |
| 5. Disodium EDTA | 0.1 | Dissolvine Na2/Akzo Nobel Chemicals, Inc. |
| 6. EthylHexyl Methoxycinnamate sunscreen | 7 | Neo Heliopan AV/Haarmann & Reimer |
| 7. Butyl Methoxydibenzoylmethane sunscreen | 2 | Neo Heliopan 357/Haarmann & Reimer |
| 8. 4-Methylbenzylidene Camphor sunscreen | 3 | Neo Heliopan MBC/Haarmann & Reimer |
| 9. Cyclomethicone | 3 | Dow Corning ® 345 FLUID |
| 10. C12-15 Alkyl Benzoate | 5 | Finsolv TN/Witco Corporation |
| 11. C15-19 Alkane | 3 | Gemseal 40/Total |
| 12. Dow Corning waxy cyclopolysiloxane containing alkyl substituents and Aryl substituents | 5 | |

The emulsifier (1) was added to water (2) under strong agitation and mixed for 10 minutes. Ingredients (3) to (5) were added while continuing mixing and the aqueous mixture was heated to 80° C. The waxy cyclopolysiloxane (12) was melted at 80° C. and blended with the sunscreens (6 to 8). The resulting blend was emulsified in the hot aqueous mixture. The diluents (9 to 11) were mixed into the emulsion and homogenised in a Silverson (Trade Mark) mixer.

EXAMPLE 11

A hand and body lotion was prepared by combining the following components

TABLE 6

| Ingredient | Wt. % | Supplier/Trade Name |
|---|---|---|
| 1. Stearic acid | 2 | Henkel-Emery ® 120 |
| 2. Glyceryl stearate, PEG-100 stearate | 2 | Uniqema-Arlacel ® 165 |
| 3. Cetyl alcohol | 3 | Henkel-Lanette ® 16NF |
| 4. Mineral oil | 5 | Crompton-Carnation ® White Mineral Oil |
| 5. Waxy cyclopolysiloxane containing long chain alkyl substituents | 4 | |
| 6. Vitamin A palmitate | 1 | Roche-Retinyl Palmitate |
| 7. Deionized Water | 77.2 | |
| 8. Glycerin | 5 | Fisher Chemicals-Glycerin |
| 9. Triethanolamine | 0.8 | Fisher Chemicals-Triethylamine |

The aqueous phase consisting of glycerin (8), triethanolamine (9), and water (7) was combined and heated to 70° C. The waxy cyclopolysiloxane (5) and retinyl palmitate (6) were melted at 70° C., mixed together, and added to the heated aqueous phase. The Emery® 120 (1), Arlacel® 165 (2), Lanette® 16NF (3) and Carnation® white mineral oil (4) were melted (~70° C.) and mixed using a Lightnin® mixer (~1376 rpm). The water phase with the waxy cyclopolysiloxane and retinyl palmitate was slowly added to ingredients 1-4 and mixed until homogenous. The mixing was continued for 15 minutes and then the batch was cooled to room temperature with continued mixing.

This procedure was repeated using vitamin E in place of the retinyl palmitate.

The procedure was also repeated using a vitamin mixture of Vitamin A, Vitamin E and Vitamin C in caprylic/capric triglycerides (sold by BASF as RetiSTAR®) replacing the retinyl palmitate.

In all three experiments release of the vitamin was controlled by the waxy cyclopolysiloxane.

EXAMPLE 12

The process of Example 11 was repeated using a waxy cyclopolysiloxane containing aryl substituents as well as alkyl substituents in place of the wax used in Example 11. Release of the vitamin was controlled by the waxy cyclopolysiloxane.

EXAMPLE 13

A facial moisturizer with sunscreen composition was prepared by combining the following components

TABLE 7

| Ingredient | Wt. % | Supplier/Trade Name |
|---|---|---|
| 1. Glycerin | 4 | Fisher Chemicals-Glycerin |
| 2. DM DM Hydantoin | 0.3 | Lonza-Glydant ® |
| 3. Deionized Water | 77.7 | |
| 4. Octyl Methoxcinnamate | 5 | BASF-Uvinul ® MC 80 |
| 5. Dimethicone, Dimethicone Crosspolymer | 5 | Dow Corning-9041 |
| 6. Dow Corning ® waxy Cyclopolysiloxane alkyl substituents and aryl substituents | 4 | |
| 7. Vitamin A Palmitate or Vitamin E or Vitamin A, Vitamin E, Vitamin C in Caprylic/Capric Triglycerides | 1 | Roche-Retinyl Palmitate Roche-Tocopherol BASF-RetiSTAR ® |
| 8. Polyacrylamide, $C_{13-14}$ Isoparaffin, Laureth-7 | 3 | Seppic-Sepigel ® 305 |

The water phase consisting of glycerin (1), Glydant (2), and water (3) was blended using a Lightening® mixer (~300 rpm). Ingredients (4) to (5) were added while continuing mixing and the mixture was heated to 80° C. The waxy cyclopolysiloxane (6) and retinyl palmitate (7) were melted at 80° C. and blended with ingredients (1 to 5). The Sepigel® 305 was added to the mixture and the Lightnin® mixer speed was increased (~1376 rpm) with the thickening of the emulsion. The mixing was continued for 10 minutes and then the batch was cooled to room temperature with continued mixing.

This procedure was repeated using vitamin E in place of the retinyl palmitate and also with the vitamin mixture (RetiSTAR) replacing the retinyl palmitate.

In all three experiments release of the vitamin was controlled by the waxy cyclopolysiloxane. These experiments were not designed to control release of the Octyl Methoxycinnamate by the waxy cyclopolysiloxane.

EXAMPLE 14

A silicone wax was prepared by reacting an olefin mixture (C26-C45 alkyl chain length) with tetramethylcyclotetrasiloxane to form a cyclic poly(methylalkylsiloxane) wax.

An aqueous thickening solution was prepared by dispersing 3.51 g xanthan gum (Keltrol RD (Trade Mark) and 9.66 g hydroxyethylcellulose (Natrosol 250 LR(Trade Mark)) in 382.64 g of demineralised water and adding. 0.69 g sorbic acid, 1.36 g benzoic acid and 3.15 g of a 10% solution of sulfuric acid.

47 g of the thickening solution, 4.5 g of Volpo (Trade Mark) S2 and 3.9 g of Volpo S20 ethoxylated stearyl alcohol non-ionic surfactants, 14.3 g of sodium chloride, 26 g of Arquad 16-29 and 57.4 g of the silicone wax were loaded in a stirred reactor and heated to 80° C. 14.42 g of the highly volatile perfume mix was then added. After 20 minutes, the heating was stopped. 31 g of the thickening solution followed by 104 g of demineralised water were finally added to form an emulsion of a blend of perfume and wax in weight ratio 1:4.

EXAMPLE 15

62.6 g of the thickening solution, 6 g of Volpo S2, 5 g of Volpo S20, 18.6 g of sodium chloride, 34.5 g of Arquad 16-29 and 84.5 g of the cyclic poly(methylalkylsiloxane) wax of Example 14 were loaded in a stirred reactor and heated to 80° C. 11.08 g of the highly volatile perfume mix was then added. After 20 minutes, the heating was stopped. 41 g of the thickening solution followed by 137 g of demineralised water were finally added to form an emulsion of a blend of perfume and wax in weight ratio 1:7.6.

The emulsions of Examples 14 and 15 were each incorporated in a rinse cycle fabric softener at a level corresponding to 3% perfume in the softener. They were evaluated in a Miele 934 front loading washing machine, loaded with 4 terry towels and 5 pillowcases. For the main wash at 40° C., 30 g of a detergent powder and 17 liters of water were used. The softener was incorporated in the rinse. After line drying, the odor of the towels was followed for eight days. Example 15 was found to give more intense odor during the 8 days of testing than Example 14, demonstrating that for this perfume used in a rinse cycle, a 1/7.6 perfume/wax provides a better control of fragrance release than the 1/4 ratio.

EXAMPLE 16

59.5 g of the thickening solution, 30 g of esterquat cationic surfactant (Tetranyl L1/90 (Trade Mark)), 33 g of Arquad 16-29 and 64 g of the cyclic poly(methylalkylsiloxane) wax of Example 14 were loaded in a stirred reactor and heated to 80° C. to form an oil-in-water emulsion. 15.8 g of a highly volatile perfume mix was then added to the emulsion. After 20 minutes, the heating was stopped. 37.5 g of the thickening solution followed by 129 g of demineralised water were finally added. The product was an emulsion of a blend of perfume and wax in weight ratio 1:4.

The emulsions of Examples 15 and 16 were compared according to the same protocol as Examples 14 and 15. This time, the Example 16 emulsion of 1/4 perfume/wax ratio gave a more sustained odor than Example 15, showing the advantages of the use of esterquats.

EXAMPLE 17

A silicone wax was prepared by reacting an olefin mixture (C26-C45 alkyl chain length) with tetramethylcyclotetrasiloxane to form a cyclic poly(methylalkylsiloxane) wax.

An aqueous thickening solution was prepared by dispersing 3.51 g xanthan gum (Keltrol RD (Trade Mark) and 9.66 g hydroxyethylcellulose (Natrosol 250 LR(Trade Mark)) in 382.64 g of demineralised water and adding. 0.69 g sorbic acid, 1.36 g benzoic acid and 3.15 g of a 10% solution of sulfuric acid.

62.6 g of the thickening solution, 6 g of Volpo S2, 5 g of Volpo S20, 18.6 g of sodium chloride, 34.5 g of Arquad 16-29 and 84.5 g of the silicone wax were loaded in a stirred reactor and heated to 80° C. 11.29 g of a highly volatile perfume mix was then added. After 20 minutes, the heating was stopped. 41.2 g of the thickening solution followed by 137 g of demineralised water were finally added to form an emulsion.

The emulsion was incorporated into a shower gel comprising the ingredients (%) shown in Table 8 below:

TABLE 8

| | |
|---|---|
| Empicol ESB-3 (Trade Mark) surfactant | 30 |
| Oramix NS 10 (Trade Mark) surfactant | 5 |
| Amonyl 380 BA (Trade Mark) surfactant | 10 |
| Brij 30 (Trade Mark) surfactant | 2 |
| Sepigel 305 | 2 |
| Emulsion of Example 17 | 17.73 |
| Water | 33.27 |
| KOH (10%) | q.s. |

Panelists were treated with two shower gels: one with the emulsion of Example 17 as described above or a control comprising 0.5% free perfume. The perfume intensity on their forearms were evaluated on a scale of 1 to 20 (20 is highest intensity). The results are shown in Table 9

TABLE 9

| | Odour after 2 minutes | Odour after 1 hour | Odour after 3 hours | Odour after 5 hours |
|---|---|---|---|---|
| control | 0 | 4 | 2 | 1 |
| Shower gel of Example 17 | 18 | 13 | 15 | 16 |

The same two composition was applied on hair as shampoo. Panelists were asked to evaluate the perfume intensity on the hair. The results are shown in Table 10 below

TABLE 10

| Time (hours) | Control | Example 17 |
|---|---|---|
| 0 | 3 | 15 |
| 2 | 1 | 17 |
| 4 | 0 | 18 |
| 6 | 1 | 15 |

The invention claimed is:

1. A composition for controlling the release of an active material selected from fragrances, sunscreens, vitamins, drugs, biocides, pest repellents, catalysts and cooling agents, from a cleaning composition, household care product or textile treatment composition, comprising a blend of the active material and a waxy silicone material, wherein the blend of active material and waxy silicone material is in an emulsion form, and that the waxy silicone material has a melting point 10-200° C., that the waxy silicone material comprises a cyclopolysiloxane in which at least 20 percent of the silicon atoms in the cyclopolysiloxane have an alkyl substituent having 16 to 100 carbon atoms, and that 10 to 80 percent of the silicon atoms of the cyclopolysiloxane have a silicon bonded substituent of the formula X—Ph, wherein X denotes a divalent aliphatic organic group bonded to silicon through a carbon atom and Ph denotes an aromatic group.

2. The composition according to claim 1 in which 50-80 percent of the silicon atoms in the cyclopolysiloxane wax have an alkyl substituent containing 16 to 100 carbon atoms, and 20 to 50 percent of the silicon atoms of the cyclopolysiloxane wax have a silicon-bonded substituent of the formula X—Ph.

* * * * *